(12) United States Patent  
Apotheker et al.

(10) Patent No.: US 7,392,810 B2
(45) Date of Patent: Jul. 1, 2008

(54) DENTAL FLOSSING CARTRIDGE SYSTEM AND DRIVER ATTACHMENTS

(76) Inventors: Harvey Apotheker, 613 Patriots Rd., Templeton, MA (US) 01468; Robert N. Ross, 563 Whitney St., Gardner, MA (US) 01440

( * ) Notice: Subject to any disclaimer, the term of this patent is extended or adjusted under 35 U.S.C. 154(b) by 103 days.

(21) Appl. No.: 11/368,085

(22) Filed: Mar. 3, 2006

(65) Prior Publication Data

US 2007/0204878 A1    Sep. 6, 2007

(51) Int. Cl.
*A61C 15/00* (2006.01)
(52) U.S. Cl. .................... 132/323; 132/322; 132/329
(58) Field of Classification Search ............ 132/322, 132/323–329
See application file for complete search history.

(56) References Cited

U.S. PATENT DOCUMENTS 3,902,510 A * 9/1975 Roth ...................... 132/322
4,326,549 A * 4/1982 Hinding .................. 132/322
5,184,632 A * 2/1993 Gross et al. ............. 132/326
5,207,773 A * 5/1993 Henderson .............. 132/322
5,913,418 A * 6/1999 Singh ..................... 206/63.5
2007/0006402 A1* 1/2007 Kang ..................... 15/22.1

* cited by examiner

*Primary Examiner*—Robyn Doan

(57) ABSTRACT

A new dental flossing system comprising; a.) Multiple compact floss dispensing cartridges having quick attachment means to a driver to advance floss contained within said floss dispensing cartridge, b.) A packaging container for multiple said compact floss dispensing cartridges and c.) Drive extension attachment means to configure new and existing dental drivers for use with said compact floss dispensing cartridges. The unique features built into said compact floss dispensing cartridge comprise; a plaque accumulator, containment of additive materials to the floss before use, and floss tension control. Novel system features built into said drive extension attachment means comprise; a self-locking gear train, auxiliary motion to said compact floss dispensing cartridge and quick attachment means to said compact floss dispensing cartridge. The new dental flossing system enhances the use of dental floss materials and dental drivers to advance floss and to remove plaque without depositing collected plaque on to other teeth.

22 Claims, 11 Drawing Sheets

DENTAL FLOSSING CARTRIDGE SYSTEM AND DRIVER ATTACHMENTS

BACKGROUND OF THE INVENTION

1. Field of the Invention

This invention relates to dental flossing systems and components that advance dental floss by use of a driver. Novel components of the new system comprise; a new compact floss dispensing cartridge having unique features therein and quick attachment means to said driver. The invention also includes drive extension means to configure existing drivers to advance floss contained within said compact floss dispensing cartridge. The new system further consists of a dedicated storage container that holds multiple said compact floss dispensing cartridges.

2. Description of Related Art

The use of hand held dental floss was introduced by Levi Spear Parmly in 1815, who used a silk thread to floss in between teeth. Although the materials have changed over the years, hand held dental flossing is still the most effective method of removing plaque and food particles trapped within interdental spaces and subgingival areas. Trained dental professionals are best at instructing flossing by hand. The preferred method utilizes 18-24 inches of floss wound around fingers. A small segment of the floss is pressed or worked in between teeth. The floss is then moved back and forth as well as up and down to remove plaque and trapped food particles. The floss is then repositioned so that a new section of floss is used for cleaning in between each space to prevent collected plaque from being re-deposited on to other teeth, interdental spaces or subgingival areas. The act of hand flossing is a bit awkward for many people to administer on themselves; it is especially hard to position fingers in the posterior regions of the oral cavity to floss in between molars. Many users will redeposit collected plaque onto other teeth if they do not utilize different portions of the string for cleaning each interdental space. There are many manufacturers of floss string, threads and tapes, each material providing unique features and properties. There are different sizes, material types, textures and flavors available to serve numerous intended markets.

Plaque and food particles collected on used dental floss materials contain a high level of bacteria. For sanitary considerations, it is desirable that used floss string be disposable. Likewise, it is also desirable for portions of a flossing device that are exposed to used floss be disposable.

There are popular flossing devices currently being offered in the marketplace having a compact removable two-pronged component that supports a fixed length segment of floss in between both prongs. One such product is offered under the trademark "Reach". This device improves the ability to reach into the back portions of the oral cavity and can dislodge trapped particles of food and large portions of plaque. The use of a single fixed length segment of floss to remove plaque from multiple teeth during a flossing session causes a fundamental problem. The fixed length segment of floss will collect plaque from the first space cleaned between teeth and can then redeposit the plaque onto subsequent teeth, interdental spaces and subgingival areas cleaned.

Other devices add vibratory movement to the pronged component having a fixed length of floss, one such product described in U.S. patent D493,577 S to Winkler is currently offered in the market place under the trademark "Hummingbird". U.S. Pat. No. 5,411,041 to Ritter provides improved action to a fixed length of floss. Applying movement to the fixed length of floss can assist in the loosening of particles trapped in between teeth and can even assist in the massaging of gingival tissue, however the same problem in removing plaque and re-depositing plaque to other teeth still exists.

U.S. Pat. Nos. 5,217,031 to Santoro, and 5,613,508 to Bushman both disclose devices using a motor drive to translate floss. Motor translation of floss described in these patents improves upon the application of floss via a device. In these patents, portions of the device that are exposed to used floss are not removable. Proper sanitation of used floss and components that are exposed to used floss is not properly addressed. The orientation of the prongs that support the segment of floss described in both patents are inline with the handle portion, making it more difficult for the device to reach in the spaces between back molars.

U.S. Pat. Nos. 6,526,994 B1 to Santoro and 5,769,102 to Zebuhr, both disclose motorized flossing systems and have removable attachments. Both designs require long lengths of moving floss that must travel through elaborate paths. Removable portions of the device are not intended to be compact. The removable portions and their mechanisms cannot fit within a small confined space within the oral cavity. Portions of the device that come into contact with the mouth and used floss are not conducive to compact economical fabrication and do not merit single session use prior to discarding.

In the current market, there are many existing motorized drivers used for dental care. Typical motorized drivers used in dental offices provide a variable speed rotary shaft output powered either pneumatically or electrically. There are other drivers commonly used in home dental care. One popular driver intended for home dental care generates a short stroke, high frequency, linear, back and forth, shaft output motion that is electrically powered. Another popular driver used for dental care generates a high frequency, vibratory, side-to-side output motion to the end of a distal protruding post. These and other practical dental motor drivers are typically equipped with removable attachments and accessories, including; toothbrush attachments, polishing head attachments and some include compact fixed length flossing attachments.

A new and practical flossing attachment such as a compact cartridge, containing floss that is advanced by a driver and can be adapted for use with existing drivers is needed. The novel idea would enhance the general utility of dental motor drivers, and would improve the application and performance of dental flossing materials. A further enhancement would include a method to administer antiseptics or medicinal materials onto the floss just before use. Another further enhancement would include the addition of auxiliary motion to the working floss to simulate hand flossing. In addition, a further enhancement would include pressure-controlled activation of the driver by the dentition during use.

BRIEF SUMMARY OF THE INVENTION

Therefore, it is an object of this invention to provide a new dental flossing system having unique components, including drivers and driver attachments comprised of novel features. The new system facilitates the ability to remove plaque and trapped food particles from interdental spaces and subgingival areas while preventing removed plaque from re-depositing onto other teeth, interdental spaces and subgingival areas, the system comprising;

1.) Multiple detachable compact floss dispensing cartridges, where each compact cartridge holds floss for a single or limited number of flossing sessions, incorporating features comprising;

i.) A plaque accumulator, to prevent collected plaque from re-depositing on to other teeth, interdental spaces and subgingival areas.

ii.) Containment of additive matter to impregnate said floss before use, for medicinal purposes and fresh breath.

iii.) Built in floss tension control, to prevent unraveling of floss due to excess side forces to exposed floss during the flossing session.

iv.) Quick attachment means of the compact floss dispensing cartridge to a dedicated driver or drive extension attachment.

2.) A dedicated driver that has direct attachment means to the compact floss dispensing cartridge and has a matching drive interface to advance floss contained in the compact floss dispensing cartridge wherein the dedicated driver is either motorized or manually activated. The dedicated driver may be configured to generate auxiliary movement to the compact floss dispensing cartridge in a plane generally parallel with interdental spaces. The dedicated driver may further be configured to have a distally positioned switch that activates the driver when the device is subjected to controlled pressures generated by the users mouth or dentition.

3.) Drive extension attachments to interface and configure new and existing motorized drivers and manually activated advancement drivers having an output motion to advance floss within said compact floss dispenser cartridge. The drive extension attachment may be configured to generate auxiliary movement to the compact floss dispensing cartridge in a plane generally parallel with interdental spaces. The drive extension attachment may further be configured to have a distally positioned switch that activates the driver when the device is subjected to controlled pressures generated by the users mouth or dentition, wherein said motorized drivers include;

i.) A motor driver independently powered, having a rotary shaft output and various modes of operation.

ii.) A motor driver independently powered, having a high frequency, short stroke, linear, back and forth shaft output motion.

iii.) A motor driver independently powered, having a high frequency, small displacement, side-to-side post output motion.

iv.) A dental office motor driver, having a shaft output motion powered either electrically or pneumatically.

4.) A packaging container for storage and dispensing of multiple said compact floss dispensing cartridges, incorporating individual seals to prevent any additive materials from drying out due to air exposure.

The new dental flossing cartridge system and driver attachments improve upon the use of flossing materials, and dental drivers. The new compact size and unique features built into the compact floss dispensing cartridge improves upon the benefits of earlier motorized floss advancement drivers by reducing their benefits as well as improved features into a confined space that may be entirely inserted into the posterior portions of the oral cavity. This invention and additional features and benefits that fall within the claims made will be more apparent and further disclosed within the detailed description of the design.

BRIEF DESCRIPTION OF SEVERAL VIEWS AND DRAWINGS

DETAILED DESCRIPTION OF THE DESIGN

The new and novel flossing system and components form a versatile design made up of four main components. The main components are; a compact floss dispensing cartridge intended for single session use, a handle with drive capabilities to advance floss within said compact floss dispensing cartridge, a drive extension capable of generating auxiliary movement to the floss dispensing cartridge, and lastly a packaging and storage container for multiple disposable floss dispensing cartridges. The unique features of the new flossing system and its components will now be described in more detail.

Figure 1:
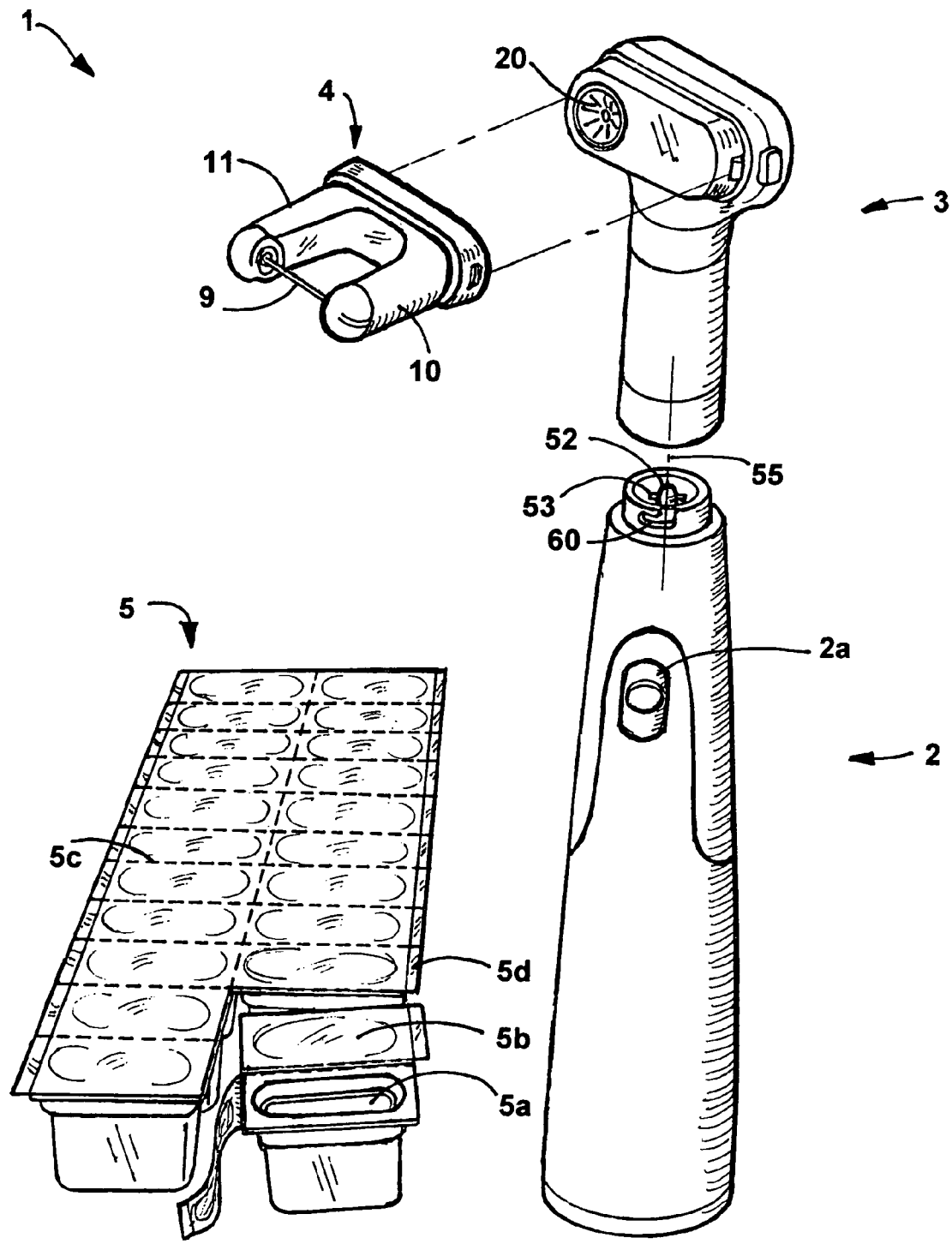
FIG. 1 is a perspective assembly of one embodiment of this invention showing; a compact floss dispensing cartridge, a drive extension, a driver handle and a packaging container for multiple compact floss dispensing cartridges.

Referring first to FIG. 1, shown is a general assembly of the primary components of the new flossing system 1. The drive handle 2 is driven by a motor and controller housed inside the drive handle 2 that is first activated by a main switch 2a. The drive extension 3 acts as an interface between the disposable floss dispensing cartridge 4 and the drive handle 2. The drive extension 3 isolates the drive handle 2 from the floss cartridge 4 and from direct contact with bacteria and plaque collected on used floss. The drive extension 3 may be directly integrated into the drive handle 2. In the preferred embodiment of FIG. 1, the drive extension 3 is removable and intended for reuse by an individual user. The drive extension 3 can be attached to the drive handle 2 to accommodate ease of access to control main switch 2a by either right or left hand operation. The drive extension 3 can also incorporate a distally positioned switch (not shown) operational either by dentition or by pressures generated by the mouth to activate floss advancement and auxiliary motions to the floss dispensing cartridges. Multiple users can each use the same drive handle 2 and remain sanitary when using their own drive extension 3. The drive extension 3 can also be used by multiple individuals and remain sanitary if the component is sterilized in between each use. It is common practice in a dentist office to sterilize devices in an autoclave chamber. The drive extension 3 will exist in diverse modifications and use different construction materials in order to satisfy different modes of use that fall within the claims of the invention.

The disposable floss cartridge 4 may be pre packaged in a packaging container 5 capable of supporting and individually sealing an array of disposable floss cartridges. The preferred packaging container 5 is made of thermally formed plastic, a cavity 5a is formed for each floss dispensing cartridge, and the opening is sealed with a removable membrane 5b. Each cavity 5a and its associated membrane 5b is separable from other cavities by a perforation 5c positioned in between each molded cavity 5a. An edge of the membrane over extends the outer edge of the container 5 in order to easily grip and separate the membrane 5b from the molded cavity 5a.

Figure 2:
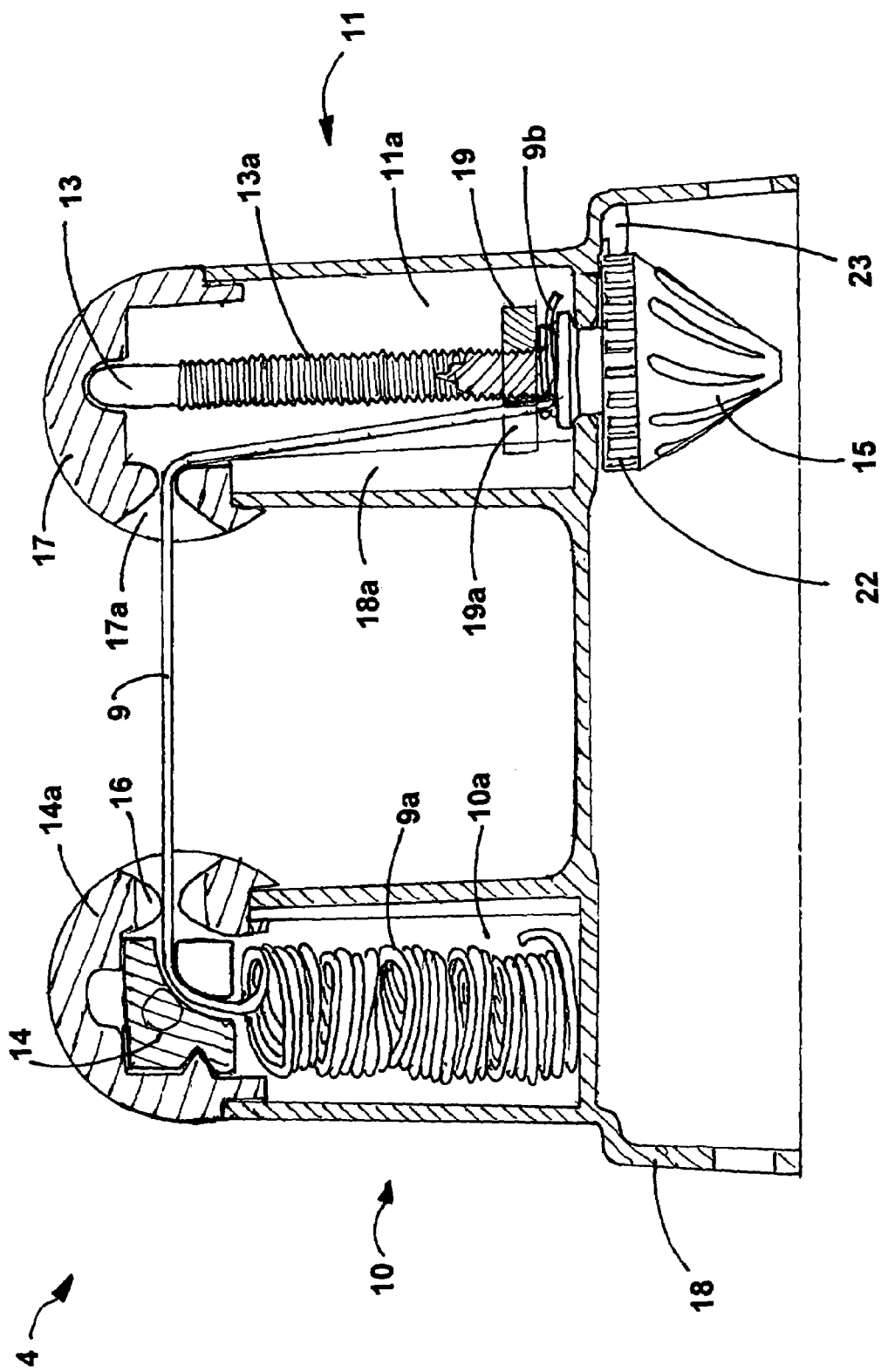
FIG. 2 is a sectional view, taken through a central plane, of one embodiment of a compact floss dispensing cartridge.

Contained within each disposable floss cartridge 4 is a length of floss initially stored within a first post 10 and a segment of exposed floss 9 spans between posts 10 and 11. The segment of exposed floss 9 is pressed between teeth to remove food particles and plaque within the space. The floss is advanced by the driver and collected into a second post 11 during use. The external enclosure and the internal mechanisms of the floss dispensing cartridge 4 can widely vary while maintaining the functional features claimed by this invention. FIG. 2 is a cross sectional view describing the functional features of one embodiment of the floss dispensing cartridge 4. Unused floss 9a is coiled and contained within an inner volume 10a located within the first post 10. The volume 10a also contains an additive material 12 to impregnate the coiled unused floss 9a. A preferred additive material 12 is a concentration of potassium nitrate providing a numbing sensation, ideal for sensitive gums. The unused floss 9a is then threaded through a friction member 14, and outer friction member 14a. The exposed floss 9 crosses an opening between both posts 10 and 11. The structural features of posts 10 and 11 within this embodiment are formed within the same outer molded housing 18. The opening dimension between posts 10 and 11 needs only to allow for minimum clearance around back molars, plus clearance to accommodate any auxiliary movements generated by the driver 2 and drive extension 3, this space is approximately 12 mm in the preferred embodiment. The exposed floss 9 is then passed through a plaque accumulator 17. The plaque accumulator 17 has an inward conical cavity to collect excess plaque from the used floss as it passes through and into post 11, thus eliminating exposure of plaque build up to the portion of the exposed floss 9 that contacts the teeth. The plaque accumulator 17 and outer friction member 14a both have external geometries that act as bumpers or guards for teeth and gums. Various methods to pull floss from post 10 into post 11 will exist including friction wheels, or meshing toothed gears to grip and pull the floss when driven by a spindle. Another method to advance the floss is described in FIG. 2; after passing through the plaque accumulator 17, the collected floss 9b is attached to the lower portion of a spindle 13 contained within the second post 11 of the disposable cartridge 4. The spindle 13 has a fine pitch thread 13a of 80-120 threads per inch. A slotted nut 19 is threaded on to the spindle 13. When the spindle assembly is secured into the outer housing 18, the slot 19a in the slotted nut 19 engages a vertical rib 18a formed in the outer housing 18, preventing the slotted nut 19 from rotating. The lower hub 15 on the spindle 13 is driven by the mating drive interface 20 shown in FIG. 1. As the spindle 13 turns, the slotted nut 19 translates up the thread 13a but does not spin. At the same time, the collected floss 9b is passing through the slot 19a and uniformly wrapping around the spindle 13 while pulling the unused floss 9a through the friction member 14. The outer friction member 14a and the plaque accumulator 17 are both retained in the outer molded body 18 by a compression press fit.

The friction member 14 provides a gripping force onto the floss 9 via a controlled crimp applied transverse to a split portion of the friction member 14 when installed into the outer friction member 14a and molded body 18. The driver can over come the friction member gripping force in order to translate the exposed floss 9 from post 10 to post 11. The resulting tension in the floss is equal to the gripping force of the friction member 14.

When the segment of exposed floss 9 of the disposable cartridge 4 is inserted into and removed from the spaces in between teeth, there can be side forces applied to the floss 9 in radial orientations normal to the axis of floss translation. If the side forces exceed the friction member gripping force there could be excess slack generated in the floss 9 in between the posts 10 and 11. To prevent excess slack in the floss due to side forces, the outer friction member 14a incorporates a locking notch 16. There are at least four radial notches where at least one notch will capture the exposed floss 9 when subjected to excessive side forces. If the side force on the floss 9 is held for a prolonged duration while the drive is still activated, the lower hub 15 of the spindle 13 is shaped to slip against the mating drive interface 20 shown in FIG. 1 of the drive extension. To prevent used floss from unraveling from the spindle assembly 13 due to excessive side forces to the floss 9, the side wall of the lower hub 15 has molded in serrations 22 that engage molded in flexure arm 23 in the molded body 18 that prevents the spindle from rotating in the reverse direction from the drive. Once any excessive side forces have been relaxed from the exposed floss 9, the floss will remain captured in the locking notch 16 until the lower hub 15 has re-gripped to the drive interface 20. The axial directional pull in the floss 9 generated when the drive is activated will dislodge the floss 9 from the locking notch 16. Other embodiments of the compact floss dispensing cartridge are also described in FIG. 9 and FIG. 10.

Figure 3:
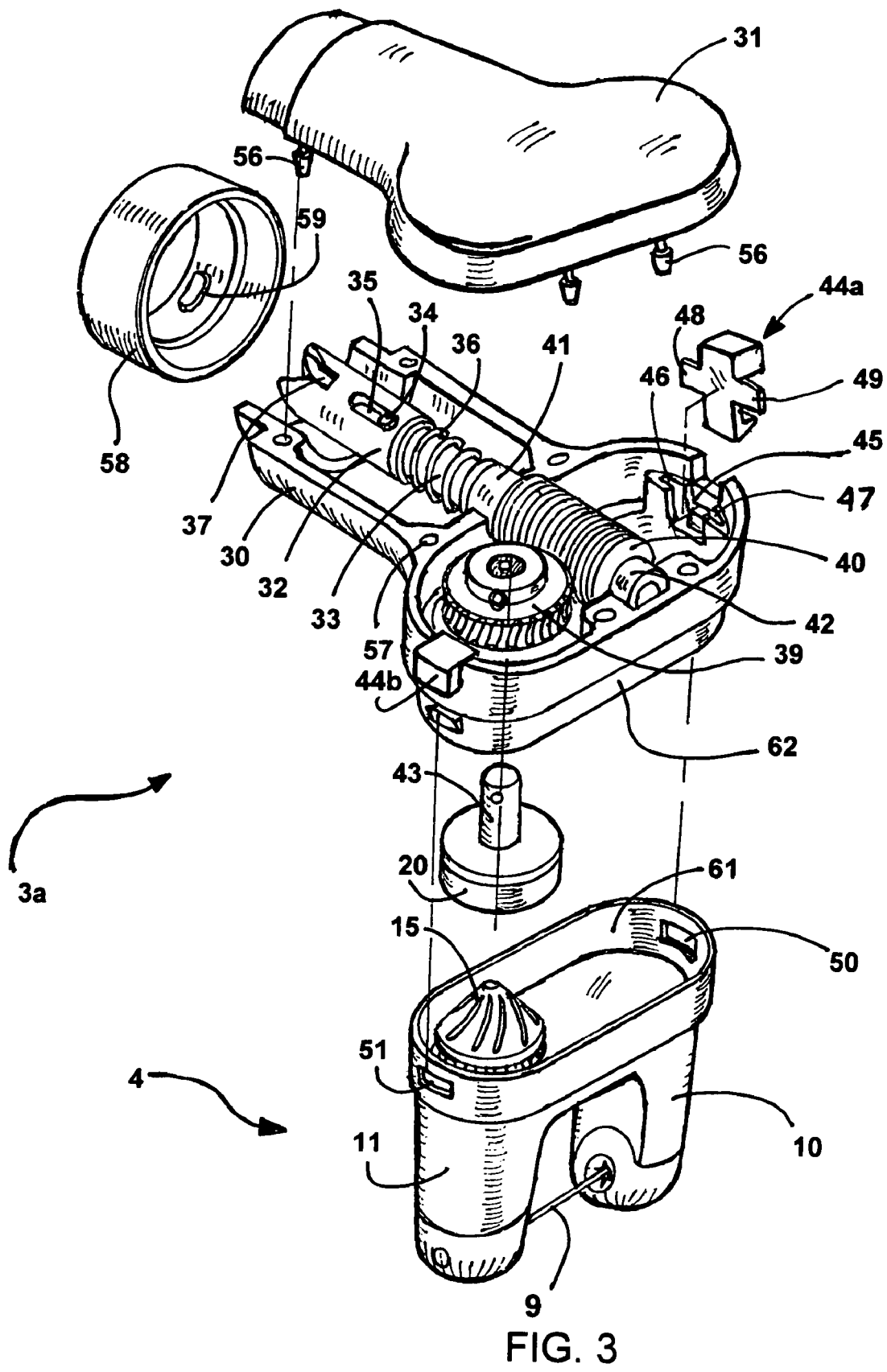
FIG. 3 is a partially exploded perspective assembly of one embodiment of a compact floss dispensing cartridge and a drive extension.

The drive extension assembly shown partially exploded in FIG. 3 accepts direct rotational drive from interfacing drivers without auxiliary movement to the floss cartridge 4. In FIG. 3, the molded outer housing halves 30 and 31 contain internal geometric features to support internal drive transmission mechanisms; a receiver sleeve 32 is pinned to the gear shaft 33 via a pin 34 through slot 35. Spring 36 provides a dynamic load against the receiver sleeve 32. The leading edge of the receiver sleeve 32 is tapered in two opposing planes from the centerline 55. A slot 37 lies in the lower portion of the tapers and facilitates self-alignment to a dedicated drive handle 2 as shown in FIG. 1. Slot 37 on the end of the receiver sleeve 32 engages a cross pin 53 in rotary drive shaft 52. The transmission gear mechanism in this embodiment of the drive extension utilizes a worm gear set, where a pinion 39 is driven by a mating helix gear 40. The worm gear provides a self locking feature to the drive train, the pinion 39 can only rotate when the helix gear 40 is rotated by the drive handle 2, therefore any undesired external forces applied to the pinion 39 will not change its radial position. The worm gear also provides a significant gear reduction potential to the higher speed driver outputs. Typical worm gear reductions ranging from 10:1 to 200:1 reduces the higher speed motor driver outputs to generate the preferred floss advancement speed of 2 to 10 millimeters per second between posts 10 and 11. Bearings 41 and 42 support the gear shaft 33. A rotary shaft 43 is mounted into the pinion 39 from under housing 30. The rotary shaft 43 contains the mating drive interface 20 that matches the lower hub 15 of the floss dispensing cartridge 4. The drive interface 20 has an inward conical shape that matches the lower hub 15 of the floss dispensing cartridge 4, to facilitate desired grip.

The push button 44a is inserted into its opening 45 on either side of the outer housing half 30. There are formed slots 46 and 47 on each side of housing halve 30 to accept spring tabs 48 and 49 on each push button 44a and 44b. The push buttons are installed in the outer housing half 30. The two housing halves 30 and 31 are aligned and fastened together via molded pins 56 in housing halve 31 and matching pin holes 57 in housing halve 30. A USP class VI adhesive is used to bond the housing halves together, as well as to bond the attachment ring 58 to secure halves 30 and 31 together. The attachment ring 58 has an internal molded protrusion 59 to bayonet fit the drive extension 3a into a keyway 60 on the dedicated drive 2 shown in FIG. 1.

Still referring to FIG. 3, firm attachment and alignment of the floss dispensing cartridge 4 to the drive extension 3a is accomplished by matched fit between internal tapered side walls 61 of the floss dispensing cartridge 4 to the external tapered walls 62 of the housing half 30. Retention of the two mating components is made by engagement of two push buttons 44a and 44b into retention slots 50 and 51 in the floss dispensing cartridge 4. The lower tapered portion of the push buttons 44a and 44b recede beneath the inner tapered sidewalls 61 of the floss dispensing cartridge 4 and into the housing 30 until the slots 50 and 51 are fully aligned over the lower portion of the push buttons 44a and 44b. Once aligned, the spring tabs 48 and 49 press the push buttons 44a and 44b into the slots 50 and 51, securing the two components together.

The used floss dispensing cartridge 4 is released from the drive extension 3a when the push buttons 44a and 44b are pressed into the housing 30, disengaging the buttons from the slots 50 and 51. Then the used floss dispensing cartridge can be discarded.

Figure 4:
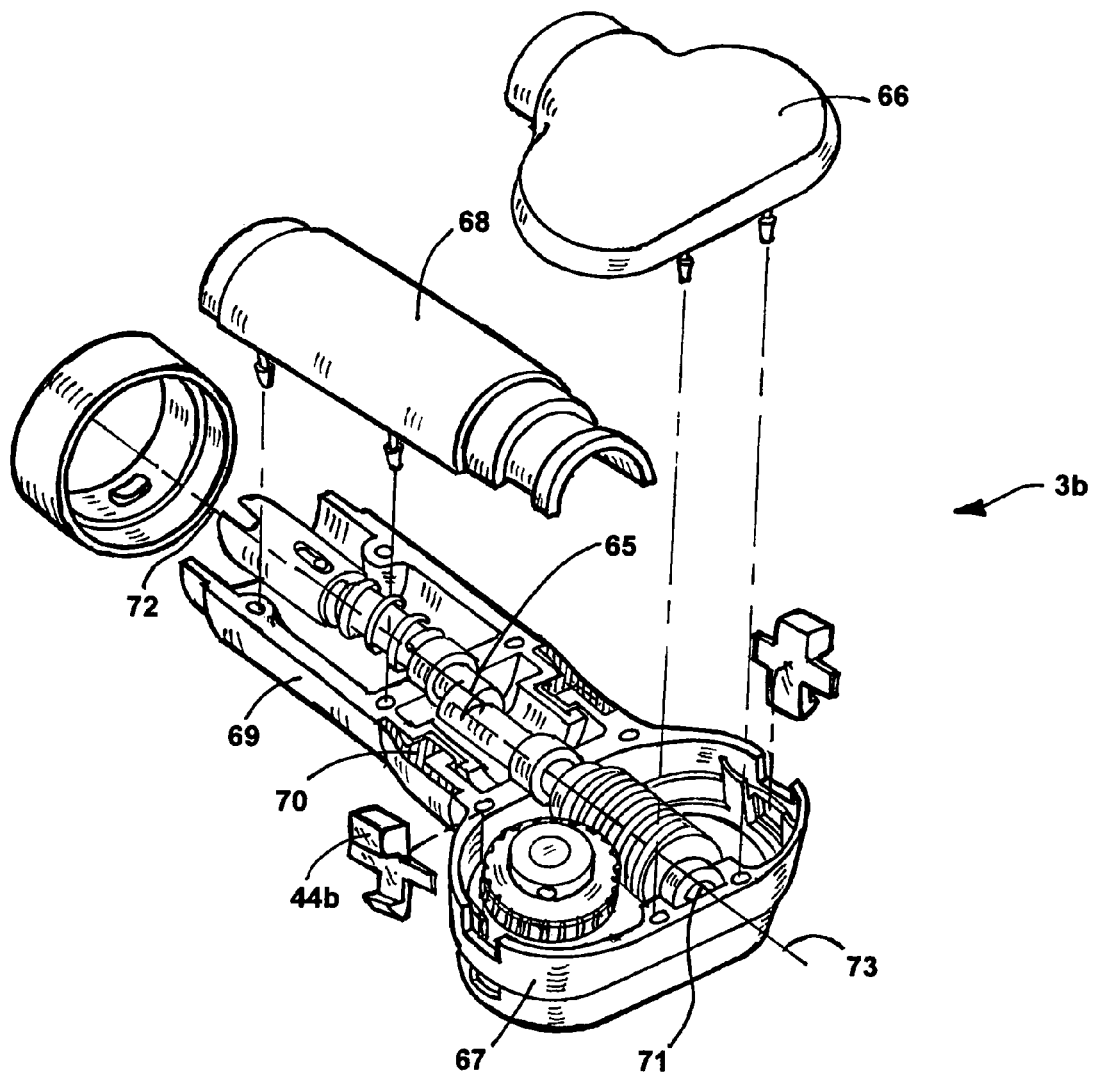
FIG. 4 is a partially exploded perspective assembly of one embodiment of a drive extension having auxiliary offset movement.

FIG. 4 is a similar embodiment to FIG. 3 with the addition of auxiliary movement to the floss cartridge. The preferred movement of the floss is back and forth and up and down within the spaces in between teeth. FIG. 4 describes the unique added features to the drive extension 3b to accomplish the desired movement to the floss in contact with teeth. The drive shaft 65 has two parallel axes 72 and 73 that are offset to obtain the desired amount of movement to the floss dispensing cartridge 4 as shown in FIGS. 1 and 2, when attached. The housing for the drive extension is made up of four molded sections. Housing sections 66 and 67 join each other and encapsulate components in direct axial alignment with axis 73 of the drive shaft 65. Housing sections 68 and 69 join each other and encapsulate the remaining portion of the assembly in direct axial alignment with axis 72 of the drive shaft 65. Housing sections 68 and 69 engage over housing sections 66 and 67 loosely interlocking both housing portions together and providing clearance for them to displace relative to each other by the drive shaft axis offset. The seam between the two moving housing portions is covered with an elastomer band 70 (shown in sectional view). The elastomer band 70 is bonded to each housing section, but not bonding the dynamic joint. The engagement to the drive is the same as described in FIG. 3 and the transmission gear utilizes a worm gear that is the same configuration as FIG. 3.

Figure 5:
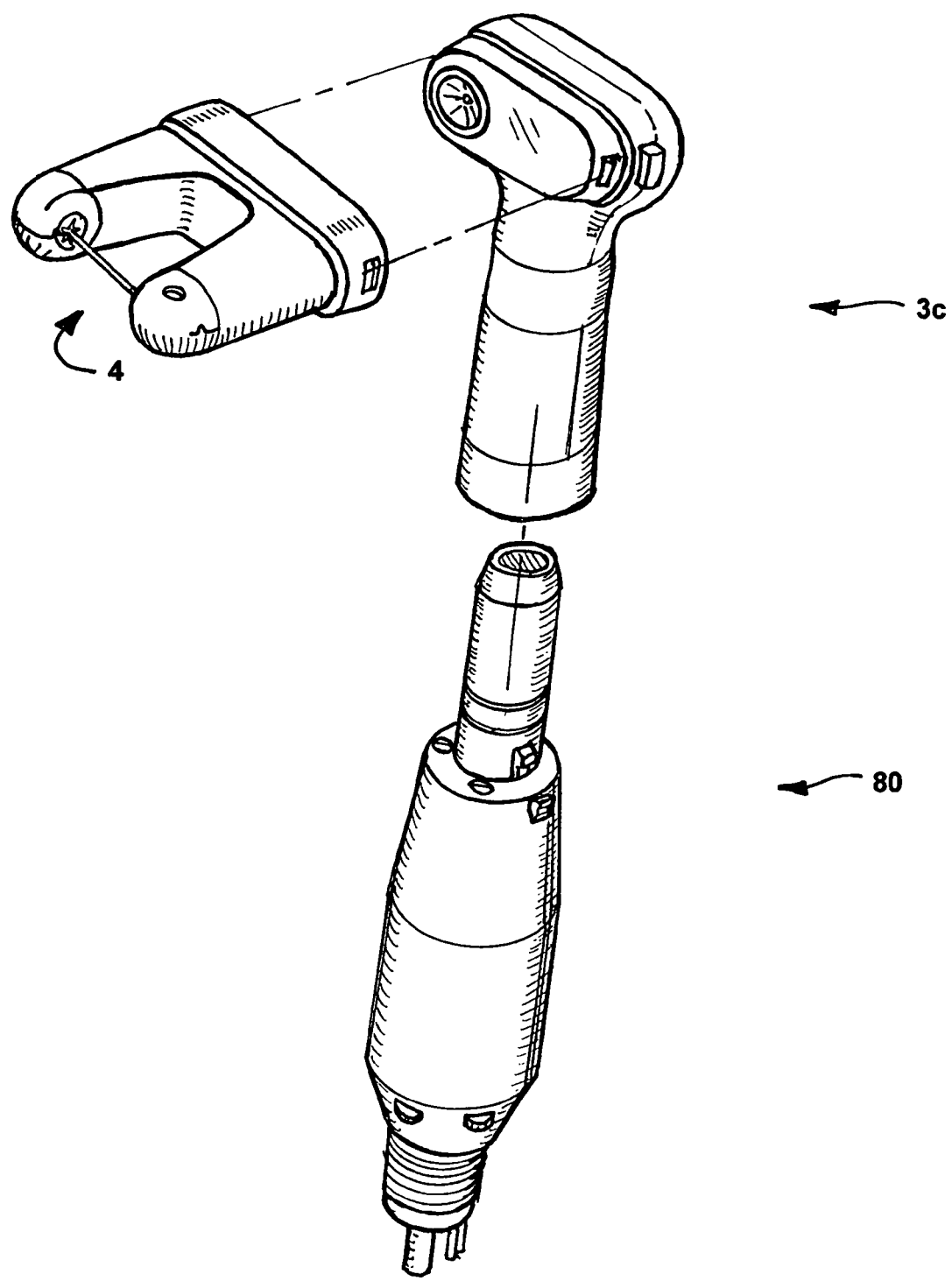
FIG. 5 is a perspective view of one embodiment of this invention showing; a compact floss dispensing cartridge, a drive extension and a dental office handle driver.

Other drivers that provide rotary motion and can be utilized to drive the drive extensions and floss cartridges embodied in FIGS. 2, 3, and 4 are pneumatic and electric dental office drivers. FIG. 5 shows one embodiment of the drive extension 3b attached to standard dental office drivers. The dental office driver 80 is sterilizable in autoclave; the drive extension 3c is sterilizable in autoclave for repeated use by multiple patients.

The floss dispensing cartridge 4 is disposable after each patient use. The disposable floss dispensing cartridge 4 can have various antiseptics in the form of a liquid or gel, numbing agents such as small concentrations of potassium nitrate gel, or flavored liquids or gels added within volume 10a in the floss cartridge 4 as shown in FIG. 2.

Figure 6:
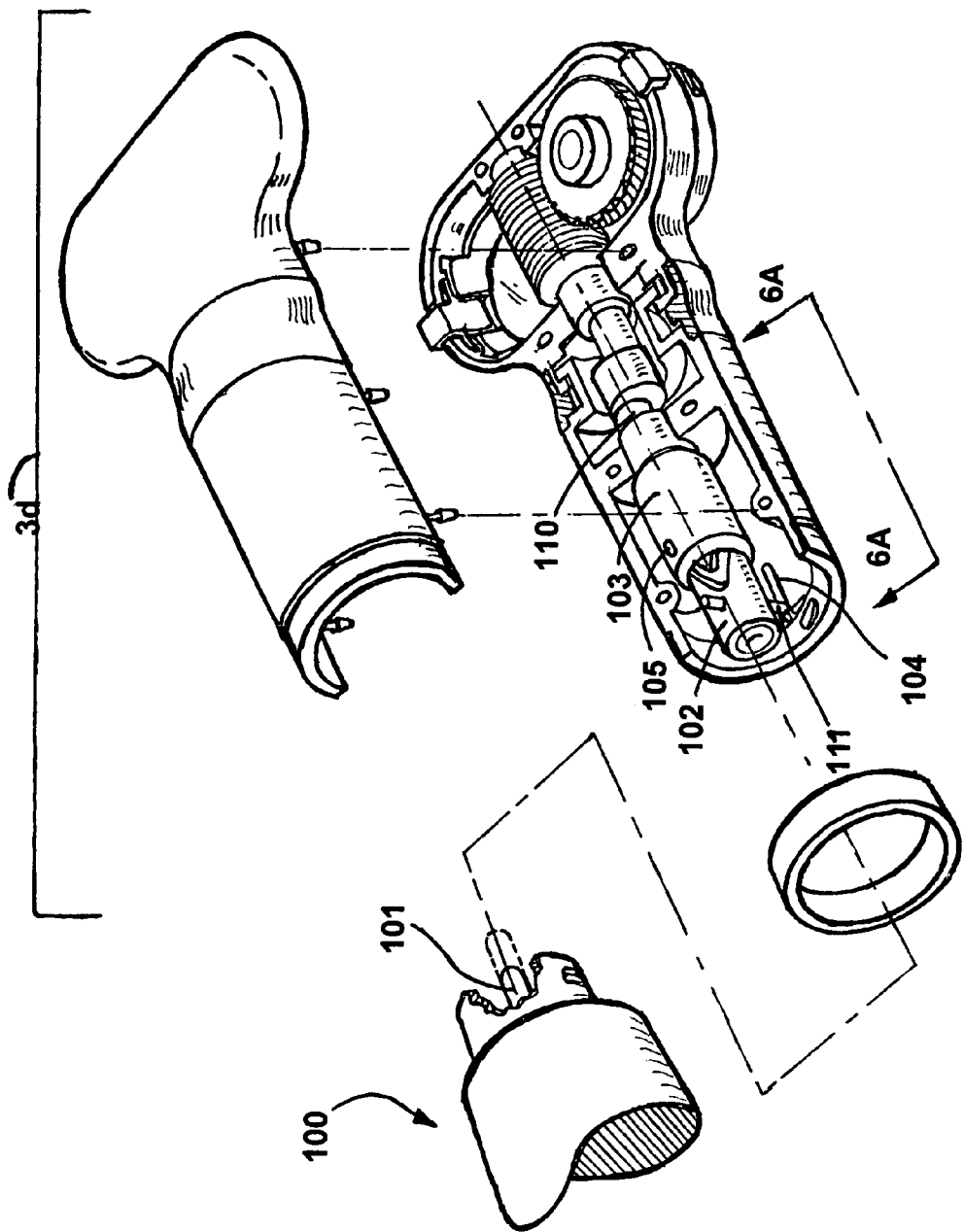
FIG. 6 is a partially exploded perspective assembly of one embodiment of this invention configured for a motor driver handle having a shaft with axial back and forth motion output.
Figure 6A:
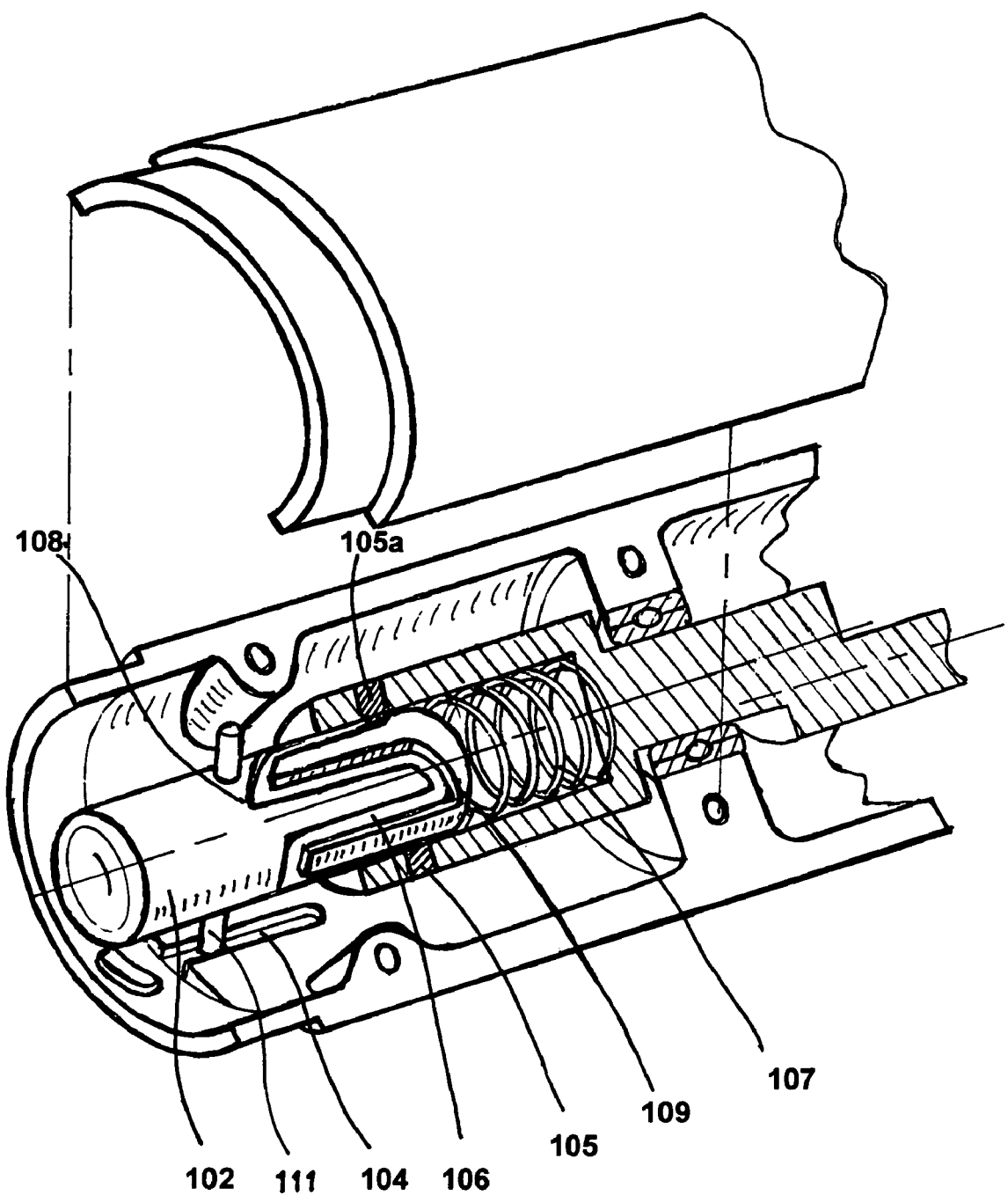
FIG. 6A is a sectional view of elements along the central axis within the drive extension shown in FIG. 6.

There are other common handle drivers used in dental applications that can be equipped to interface to the new floss dispensing cartridge. FIG. 6 describes one type of drive extension 3d that configures a driver 100 which generates a rapid back and forth movement of the drive shaft 101 along its axis. The drive extension 3d converts back and forth movement of the drive shaft 101 into an input rotation to a drive shaft 110 and to drive gears for advancing floss in floss dispensing cartridge 4 as shown in FIG. 1 when attached. Most of the components within the embodiment of FIG. 6 have been previously cited in the descriptions of FIG. 3 and FIG. 4. Therefore, only the unique components that configure the linear back and forth motion of the driver 100 into a desired rotational motion will now be described. A helix barrel 102 has a slip fit into a barrel sleeve 103; the helix barrel 102 has an anti rotation pin 111 that engages a slot 104 formed in the molded body, to prevent rotation of the helix barrel. The barrel sleeve 103 is fixedly attached to the end of a rotary shaft 110. Referring to FIG. 6A, a partial cross sectional view of the embodiment of FIG. 6, the helix barrel 102 is pinned to the barrel sleeve 103 via pins 105. Pins 105 are secured to the barrel sleeve 103 and have a clearance fit engagement into a helix track 106 that is formed within the helix barrel 102. The helix track 106 is a continuous slot around the circumference of the helix barrel 102, its path has a periodic oscillating pattern sloping in one direction to a linear extent 108 and then sloping in the opposite direction to an opposing linear extent 109. The distance between the linear extents of the helix track is shorter than the linear stroke distance of the drive shaft 101. The slope angles can vary to accommodate the desired rotational advancement with in each linear stroke of the drive shaft 101. The slope of the helix track is preferred to be in a predominantly straight linear path, parallel to the central axis of the helix sleeve 102 to accommodate the downward stroke of the motor shaft 101 allowing the helix sleeve 102 to slide back with less resistance. The straight portion in the helix track also prevents a reverse rotation in the event the motor driver is stopped during use and then restarted or re engaged. A spring 107 shown in sectional view FIG. 6A applies a constant force onto the helix barrel 102 consequently applying a force on to the pins 105 and helix track 106. Now when the motor driver 100 is activated and the output shaft 101 moves upwards toward the drive extension 3d, it pushes the helix barrel 102 into the barrel sleeve 103, pin 105 follows the helix track applying a direct rotation into the rotary shaft 110. When the motor shaft 101 moves downward away from the drive extension 3d the helix barrel 102 follows. At the linear extent of the downward stroke, the helix track leads the pin 105 into the upward slope of the helix track for the next stroke.

Figure 7:
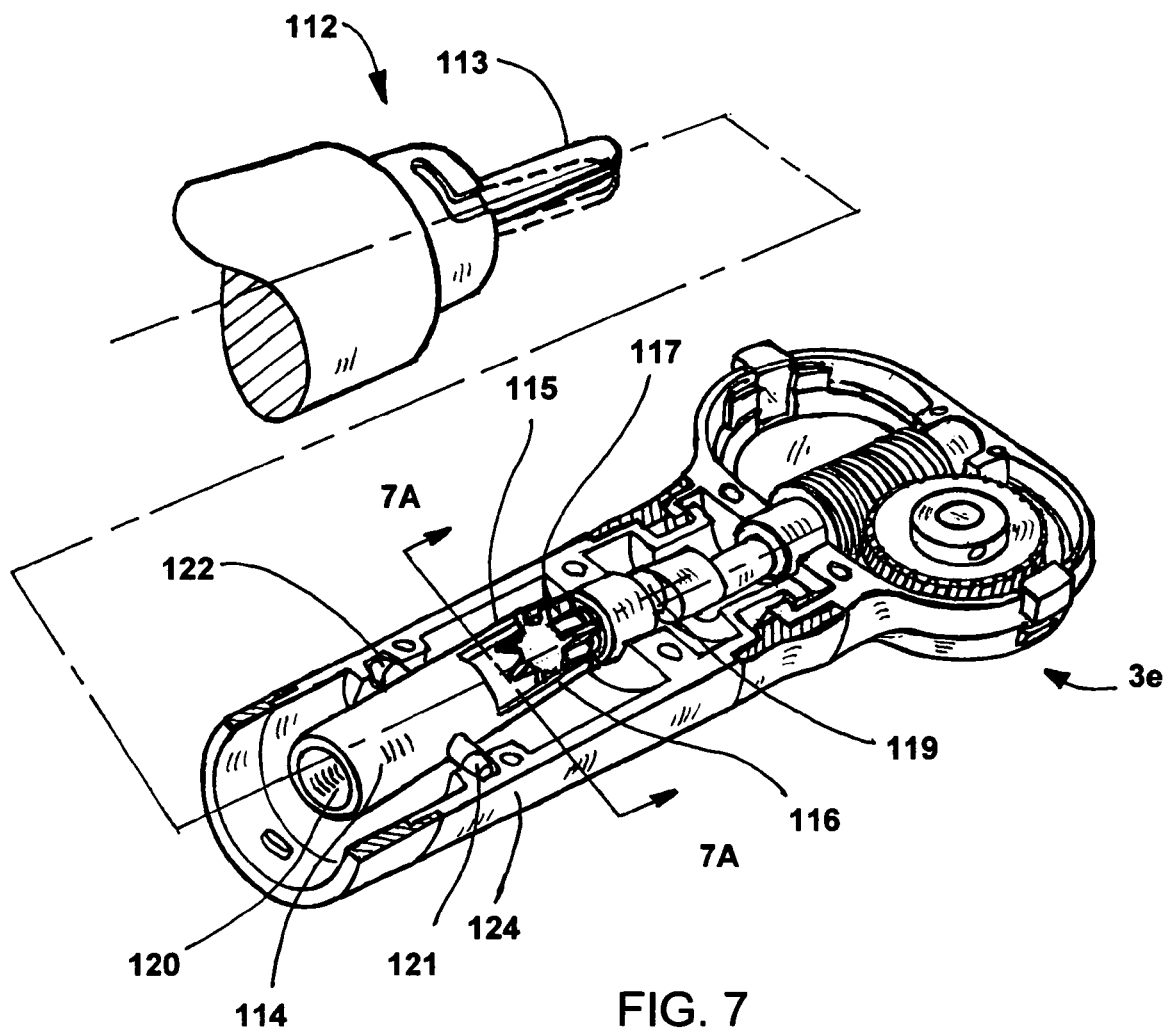
FIG. 7 is a partially exploded perspective assembly of one embodiment of this invention configured for a motor driver handle generating a side-to-side oscillating post motion output.
Figure 7A:
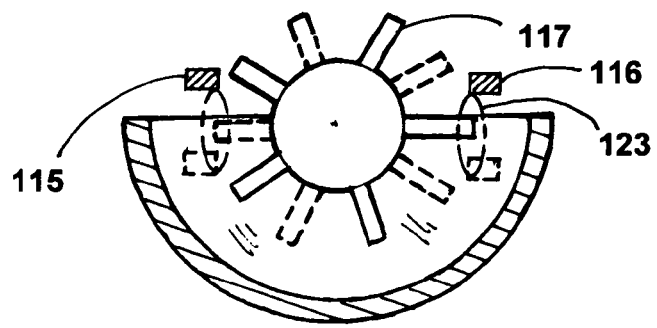
FIG. 7A is a cross sectional end view of the drive extension shown in FIG. 7.

FIG. 7 describes another driver 112 that generates a side-to-side motion of an output post 113. There is also shown a lower portion assembly of a drive extension 3e to configure the driver 112 to generate a rotary motion to drive shaft 119 for advancing floss in said compact floss dispensing cartridge 4 as shown in FIG. 1. The pivoting sleeve 114 has a bore 120 that engages the driver post 113. When the driver 112 is activated, the post 113 manipulates the pivoting sleeve 114 and a resultant movement is generated. Extension arms 115 and 116 move up and down and side-to-side about pivot posts 121 and 122. A movement 123 of the extension arms 115 and 116 as shown in FIG. 7A, are preferred to be in an elliptical path but a simpler triangular path is functional. The movement 123 in turn rotates a finned gear 117 that is fixedly attached to a rotary shaft 119 for driving the gear train for advancing floss in said compact floss dispensing cartridge 4 of FIG. 1. Now the extension 116 will engage a fin in the down stroke while extension 115 provides clearance for the finned gear to rotate, then the extension 115 will engage a fin in the upstroke while the extension 116 provides clearance for the finned gear to rotate. Movement 123 is accomplished by tapered bearing surfaces and spring loaded bearing surfaces within the bore 120, and post 113 and pivot posts 121 and 122 and pivoting sleeve 114 and surfaces in lower housing 124, shown in FIG. 7.

Figure 8:
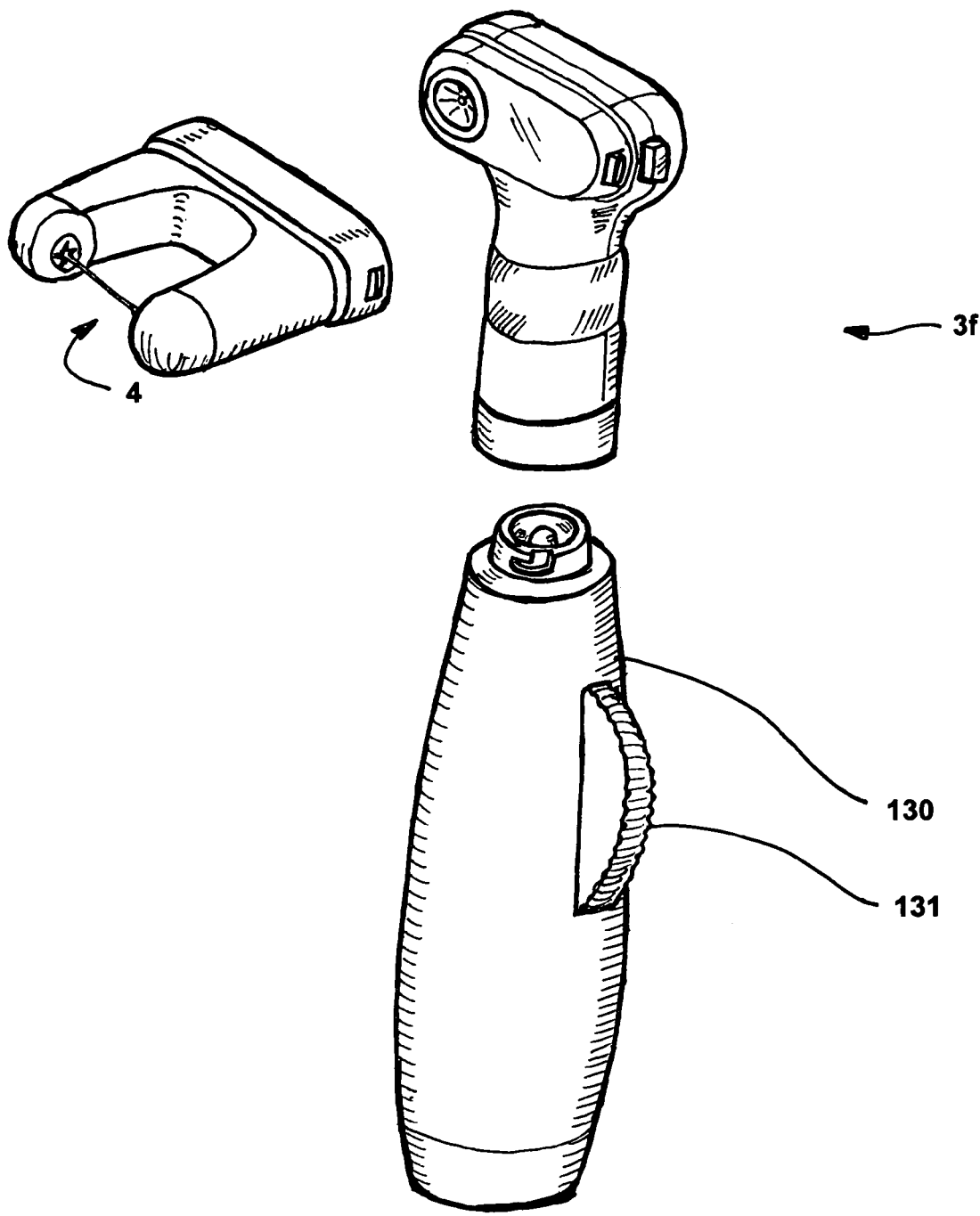
FIG. 8 is a perspective view of one embodiment of this invention showing a manually activated driver handle.

Motor drivers are not the only method of advancing floss within the floss dispensing cartridge, FIG. 8 is one embodiment of a manual driver handle 130 that generates motion to the floss dispensing cartridge 4. The manual driver 130 utilizes a series of gears driven by a first larger gear 131 whose outside diameter is partially exposed beyond the exterior portion of the handle and whose geared teeth also act as a knurled thumb grip. The operators thumb is used to turn the outside diameter of the exposed gear to wind the mechanism and to advance the floss. The drive extension 3f may be integrated into the manual driver handle in one of two orientations to accommodate convenient grip for either right or left handed operation.

Figure 9:
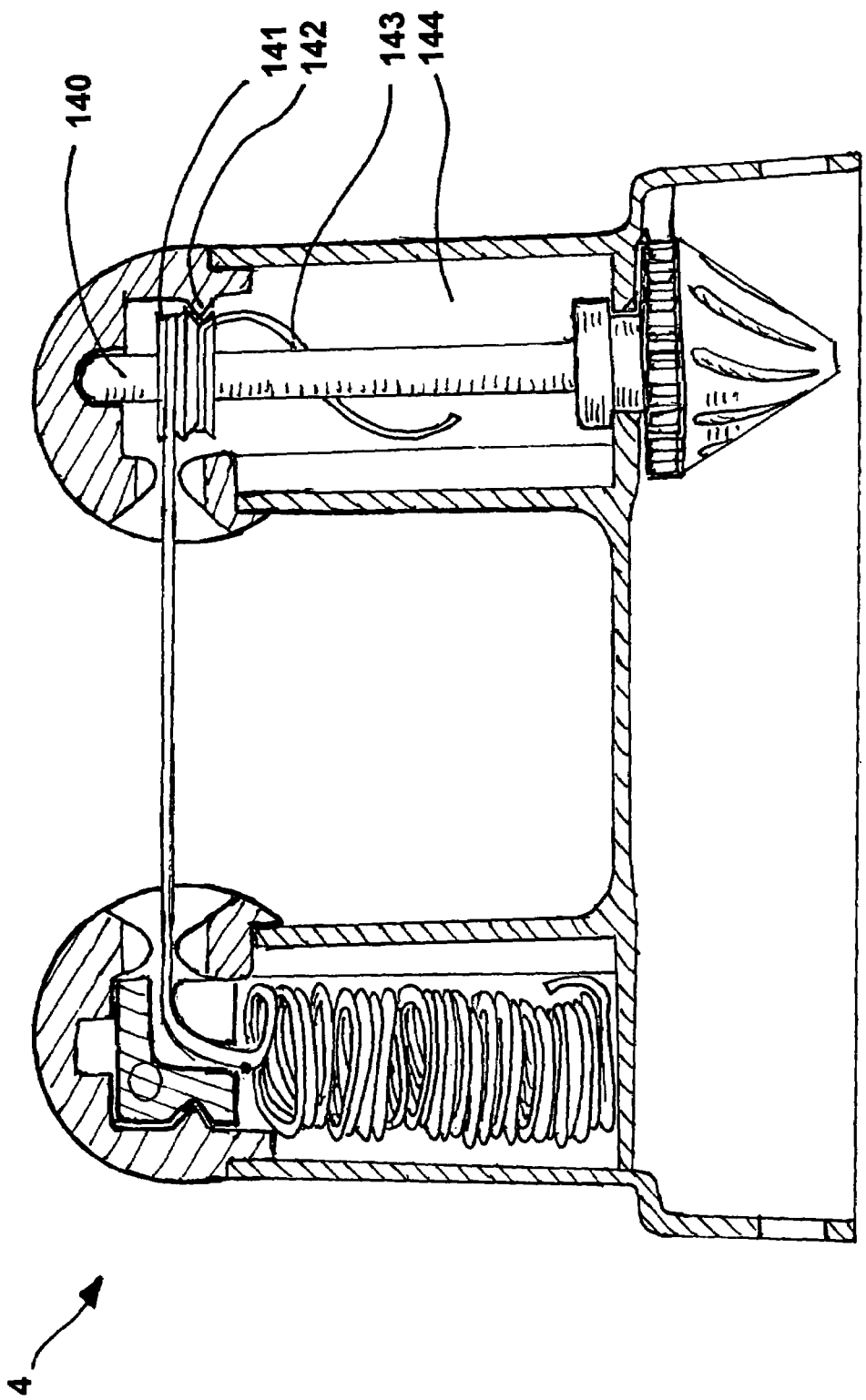
FIG. 9 is a sectional view, taken through a central plane, of an alternate embodiment of a compact floss dispensing cartridge.
Figure 10:
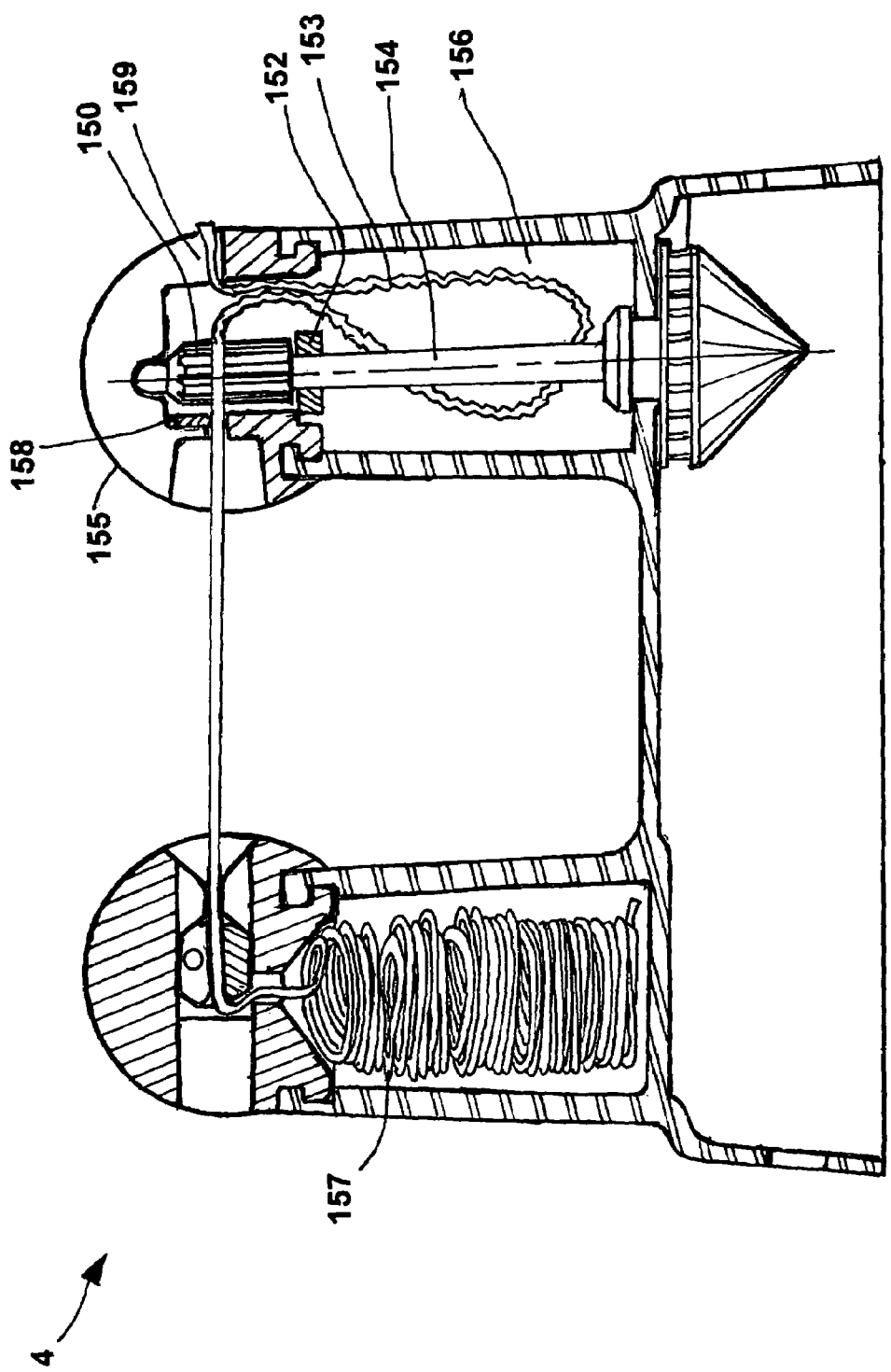
FIG. 10 is a sectional view, taken through a central plane, of a preferred embodiment of a compact floss dispensing cartridge.

To demonstrate other variations of the compact floss dispensing cartridges, FIGS. 9 and 10 describe cross sectional views of additional embodiments of the compact floss dispensing cartridge. The main differences are the mechanisms used to advance the floss utilizing different spindle assemblies; the other features not related to the spindle assemblies disclosed in the description of FIG. 2 all apply to the embodiments of FIGS. 9 and 10.

FIG. 9 depicts a spindle 140 that has a sheave 141 having multiple revolutions; a static finger 142 formed in a mating component is positioned within the lower end of the sheave 141 to extract the collected floss 143 from the sheave to be collected within the posts interior volume 144.

FIG. 10 utilizes a spindle assembly comprised of two meshing gears where gear 150 is fixed to the spindle shaft 154 and a mating gear (not shown), but in plane with gear 150, is held in position to gear 150 by a plate 152. The used floss 153 is collected and stored within the second posts interior volume 156. The preferred embodiment of FIG. 10 has an added benefit. The top cap 155 attached to a second post has a slot 159 centrally located from the top portion of top cap 155 and positioned centrally between the two meshing gears. The depth of the slot 159 extends to approximately the mid point of the meshing gear 150. When the floss is initially installed, or if the floss is broken and needs to be reinstalled in to the second post, it is first drawn from the floss supply 157 stored within a first post. A length of floss is pulled to a distance that extends beyond the width of the second post. Grabbing the end of the floss, it is then slideably installed through the open slot 159 in top cap 155 to engage in between gear 150 and its mating gear for advancement. The floss is captured between gears by a one way flexure finger 158 that deflects to allow floss to be installed, but has a rigid stop to prevent floss from being pulled out from in between gears and slot 159. Advanced floss is collected in volume 156.

Alternate embodiments of the compact floss dispensing cartridge will now be obvious, one alternate version consists of a first post that contains floss within a volume inside the first post and attachable to a drive or drive extension. The floss contained within the first post is then connectable to a separate second post wherein said second post contains a spindle assembly, such as the geared spindle assembly shown in FIG. 10 to advance floss and said second post is independently attachable to the same drive or drive extension as the first post.

An appealing alternative embodiment of the dedicated driver or drive extension incorporates a second post and portions formed within the second post including a spindle assembly, such as the geared spindle assembly shown in FIG. 10. The second post is permanently attached to the dedicated driver or drive extension. This alternative embodiment is capable of sterilization in order to kill bacteria collected on the second post after use. For this alternative embodiment the complimentary compact floss dispensing cartridge is reduced to; A compact floss dispensing cartridge sized to fit entirely within the users oral cavity, containing a length of floss initially stored within the volume of a first post and said floss dispensing cartridge having quick attachment means to a driver or drive extension. The compact floss dispensing cartridge, now a single first post, has an interior volume for additive materials, and friction gripping and locking means to the floss within the single first post similar to the friction gripping means described in FIG. 2.

It is now obvious that other drivers generating various types of output motion can be configured utilizing a drive extension into a desired output to advance floss contained within the compact floss dispensing cartridge by means of communicating mechanisms. It is also now obvious that many other embodiments of the floss dispensing cartridge can exist for use with complimentary drivers.

What we now pray to be secured by letters patent in the United States is described in the claims section.

We claim:

1. A new dental flossing system comprised of;
   a.) a compact floss dispensing cartridge sized to fit entirely within the oral cavity comprising a predetermined amount of coiled floss stored within an inner volume of a first post, a frictional gripping member positioned within said first post and engaging said floss therein, and
   b.) said system comprising a second post for collecting used said floss in a volume therein, and said second post comprising a spindle assembly for interfacing to a driver and to receive and advance said floss initially stored within said first post of said compact floss dispensing cartridge, and also
   c.) said compact floss dispensing cartridge having quick attachment means to a distal portion of said driver to advance said floss contained within said compact floss dispensing cartridge, whereby assembly of said compact floss dispensing cartridge and said distal portion of said driver fit entirely within said oral cavity for ease of flossing between teeth.

2. A system as recited in claim 1 wherein said volume of said first post contains material additives that impregnate said floss before use.

3. A system as recited in claim 1 wherein multiple, said compact floss dispensing cartridges are pre-packaged into a packaging container for bulk storage and independent attachment to said driver.

4. A system as recited in claim 1 wherein said compact floss dispensing cartridge incorporates said second post for collecting said used floss and said second post comprising a plaque accumulator for collecting removed plague from teeth, whereby said collected plaque does not redeposit onto other dentition.

5. A system as recited in claim 1 wherein said driver incorporates said second post for collecting said used floss and said second post comprising a plaque accumulator for collecting removed plaque from teeth, whereby said collected plaque does not redeposit onto other dentition.

6. A system as recited in claim 1 wherein said driver is electrically powered.

7. A system as recited in claim 1 wherein said driver is manually powered.

8. A system as recited in claim 1 wherein said driver is activated by a distally positioned switch controlled by the users dentition.

9. A system as recited in claim 1 wherein said driver generates auxiliary movement to said compact floss dispensing cartridge and said distal portion of said driver.

10. A new dental flossing system comprised of
   a.) a compact floss dispensing cartridge sized to fit entirely within the oral cavity comprising a predetermined amount of coiled floss stored within an inner volume of a first post, a frictional gripping member positioned within said first post and engaging said floss therein and
   b.) said system comprising a second post for collecting used floss in a volume therein, and said second post comprising a spindle assembly for interfacing to a drive extension and to receive and advance said floss initially stored within said first post of said compact floss dispensing cartridge, and also,
   c.) said compact floss dispensing cartridge having quick attachment means to a distal portion of said drive extension, wherein said drive extension is attachable to a driver to configure output motion of said driver to advance said floss contained within said compact floss dispensing cartridge,
   d.) whereby assembly of said compact floss dispensing cartridge and said distal portion of said drive extension fit entirely within said oral cavity for ease of flossing between teeth.

11. A system as recited in claim 10 wherein said volume of said first post contains material additives that soak into said floss before use.

12. A system as recited in claim 10 wherein multiple, said compact floss dispensing cartridges are pre-packaged into a packaging container for bulk storage and independent attachment to said drive extension.

13. A system as recited in claim 10 wherein said compact floss dispensing cartridge incorporates said second post for collecting said used floss and said second post comprising a plaque accumulator for collecting removed plaque from teeth, whereby said collected plaque does not redeposit onto other dentition.

14. A system as recited in claim 10 wherein said drive extension incorporates said second post for collecting said used floss and said second post comprising a plaque accumulator for collecting removed plaque from teeth, whereby said collected plaque does not redeposit onto other dentition.

15. A system as recited in claim 10 wherein said driver is electrically powered.

16. A system as recited in claim 10 wherein said driver is pneumatically powered.

17. A system as recited in claim 10 wherein said drive extension utilizes a self locking worm gear set.

18. A system as recited in claim 10 wherein said driver is activated by a distally positioned switch controlled by the users dentition.

19. The system as recited in claim 10 wherein said drive extension transmits auxiliary movement to said compact floss dispensing cartridge and said distal portion of said drive extension.

20. A system as recited in claim 19 wherein said auxiliary movement to said floss dispensing cartridge and said distal portion of said drive extension is in a plane generally parallel with interdental spaces within said oral cavity.

21. A system as recited in claim 10 wherein said quick attachment means comprises, a spring activated button captured within a housing portion of said drive extension and a tapered portion of said spring activated button protrudes from an opening in said housing portion of said drive extension to engage a receiving slot formed into said floss dispensing cartridge.

22. A new dental flossing system facilitating the ability to remove plaque and trapped food particles from interdental spaces and subgingival areas comprised of;
   a.) multiple disposable compact floss dispensing cartridges sized to fit entirely within the oral cavity, wherein each of said disposable compact floss dispensing cartridges comprising a predetermined amount of coiled floss stored within an inner volume of a first post, a frictional gripping member positioned within said first post and engaging said floss therein and
   b.) a second post for collecting used floss therein, and also said second post comprising a plaque accumulator for collecting removed plaque from teeth and a spindle assembly for interfacing to a drive extension and to receive said floss and advance said floss contained within said compact floss dispensing cartridge, and
   c.) said compact floss dispensing cartridge having attachable means to a distal portion of a drive extension, wherein said drive extension is attachable to a driver to configure said output motion of said driver to advance said floss contained within said compact floss dispensing cartridge and to generate auxiliary motions to said compact floss dispensing cartridge and distal portion of said drive extension,
   d.) whereby assembly of said compact floss dispensing cartridge and said distal portion of said drive extension fit entirely within said oral cavity for ease of flossing between teeth, and said system includes,
   e.) a sealed packaging container for said multiple compact floss dispensing cartridges.

* * * * *